United States Patent [19]

Hable et al.

[11] Patent Number: 5,476,959
[45] Date of Patent: Dec. 19, 1995

[54] PROCESS FOR THE PREPARATION OF DIALKYL CARBONATES

[75] Inventors: Konrad Hable, Leverkusen; Alexander Klausener, Cologne; Zoltan Kricsfalussy, Leverkusen; Heinz Landscheidt, Duisburg; Erich Wolters; Eberhard Zirngiebl, both of Cologne, all of Germany

[73] Assignee: Bayer Aktiengesellschaft, Leverkusen, Germany

[21] Appl. No.: 272,164

[22] Filed: Jul. 8, 1994

[30] Foreign Application Priority Data

Jul. 15, 1993 [DE] Germany .................. 43 23 689.8

[51] Int. Cl.⁶ .................................................. C07C 69/96
[52] U.S. Cl. .................................. 558/277; 558/260
[58] Field of Search .................................. 558/277, 260

[56] References Cited

U.S. PATENT DOCUMENTS 5,231,213  7/1993  Landscheidt et al. .................. 558/277
5,319,124  6/1994  Wolters et al. .................. 558/260
5,380,906  1/1995  Nishira et al. .................. 558/277

FOREIGN PATENT DOCUMENTS 523728  7/1992  European Pat. Off. .

OTHER PUBLICATIONS

Chinese Literature and English Abstract p. 78, 1989; "Research of a New Method of Synthesis of Dimethyl Carbonate," Xuan–Zhen et al.

Primary Examiner—José G. Dees
Assistant Examiner—Dwayne C. Jones
Attorney, Agent, or Firm—William C. Gerstenzang; Sprung Horn Kramer & Woods

[57] ABSTRACT

Dialkyl carbonates can be prepared by reacting carbon monoxide with alkyl nitrites in a continuous gas phase reaction in the presence of a heterogeneous platinum metal catalyst, the activity of this catalyst being maintained by the addition of small amounts of halogen. The dialkyl carbonates are thus formed with almost quantitative selectivity and no deactivation of the catalyst occurs.

15 Claims, No Drawings

PROCESS FOR THE PREPARATION OF DIALKYL CARBONATES

BACKGROUND OF THE INVENTION

1. Field of the Invention

The present invention relates to a process for the preparation of dialkyl carbonates by reacting carbon monoxide (CO) with alkyl nitrites in the presence of a heterogeneous platinum metal catalyst, the activity of the catalyst being maintained by the addition of small amounts of halogen.

Dialkyl carbonates are of general chemical and industrial importance. Thus, for example, diethyl carbonate is an excellent solvent in the medium boiling range. Dialkyl carbonates are also excellent carbonylating and acylating reagents. They are of great importance in the preparation of other carbonates, urethanes andureas. Finally, on account of their high oxygen content, they are suitable as fuel additives for improving the knock rating of motor fuels.

2. Description of the Related Art

It is known to prepare dialkyl carbonates by reacting phosgene or alkyl chloroformates with alcohols.

There is an increasing interest, however, in superseding the use of the toxic phosgene or the intermediates derived therefrom, such as chloroformic acid esters, by other processes.

Particularly important processes here are those in which CO is reacted in the gas phase with alkyl nitrites on heterogeneous platinum metal catalysts.

Thus, Zeitschrift für Katalytische Forschung (China) vol. 10(1) pp. 75–78 (March 1989) describes the reaction of CO and methyl nitrite on a $PdCl_2$-containing activated charcoal catalyst to form mainly dimethyl carbonate in addition to dimethyl oxalate.

In DE-OS (German Published Specification) 41 23 603, a high selectivity, based both on CO and on methyl nitrite, coupled with a high conversion, is achieved by using a heterogeneous palladium chloride catalyst with $\gamma$-$Al_2O_3$ as the support. However, to maintain the catalytic activity, gaseous hydrogen chloride must be added to the educt mixture in amounts of up to 1000 ppm (by volume). This can lead to corrosion problems if it is proposed to carry out this process on the industrial scale.

SUMMARY OF THE INVENTION

Surprisingly, it has been possible to overcome the above-mentioned disadvantages by the addition of small amounts of an elemental halogen, especially by the addition of chlorine or bromine, to the reaction mixture.

A process has been found for the preparation of dialkyl carbonates of the general formula $$O=C(OR)_2 \qquad (I),$$

wherein

R represents linear or branched $C_1$–$C_4$-alkyl, by reacting carbon monoxide (CO) with alkyl nitrites of the formula $$RONO \qquad (II),$$

wherein

R is as defined, in the presence of an inert gas, in the presence of the corresponding alcohol ROH and in the presence or absence of NO, on a heterogeneous supported platinum metal catalyst, at elevated temperature in a continuous gas phase reaction, said process being characterized in that the reaction is carried out at a volume ratio of alkyl nitrite:CO=0.1 to 10:1, preferably 0.2 to 4:1 and particularly preferably 0.3 to 3:1, a pressure of 0.5 to 10 bar, preferably 0.8 to 7 bar, particularly preferably 1 to 6 bar and very particularly preferably 1 to 5 bar, and a temperature of 50° to 170° C., preferably 70° to 160° C. and particularly preferably 70° to 150° C., halogen being added batchwise or continuously.

DETAILED DESCRIPTION OF THE INVENTION

All the supported platinum metal catalysts known to those skilled in the art are suitable for the process according to the invention, preferably supported palladium catalysts, particularly preferably supported palladium(II) halide catalysts and very particularly preferably supported $PdCl_2$-containing catalysts on supports such as aluminium oxide, spinels, silicates, montmorillonites, zeolites, activated charcoals, molecular sieves, diatomaceous earths, silicon carbide, silicon dioxide, metal oxides, metal phosphates, heteropolyacids and the like.

The reaction on which the process according to the invention is based takes place according to the following equation:

$$CO + 2RON \longrightarrow O=C(OR)_2 + 2NO$$

where R is linear or branched alkyl having 1–4 C atoms, for example methyl, ethyl, propyl, isopropyl, butyl or isobutyl, preferably methyl or ethyl and particularly preferably methyl.

While it is basically possible to react CO with an alkyl nitrite in the absence of any other component in the gas mixture, for example when the composition of the mixture lies outside the explosion limits, an inert gas is frequently used to dilute the reactants. Examples of inert gases which can be used in this way are noble gases, nitrogen and carbon dioxide, preferably argon, nitrogen and carbon dioxide and particularly preferably nitrogen and carbon dioxide.

The amount of inert gas is 20 to 80 vol %, based on the total volume of gas flowing into the reactor. The inert gas, unreacted reactant residues which may be present and other gaseous reaction aids or by-products can be recycled in the sense of a continuously operating cyclic process, as described for example in Patent Application EP 523 728, albeit in a form not wholly satisfactory in technical terms, although certain partial volumes of the circulating gas mixture are optionally withdrawn continuously or batchwise.

The volume ratio of the reactants alkyl nitrite and CO used in the reaction is 0.1 to 10:1, preferably 0.2 to 4:1 and particularly preferably 0.3 to 3:1.

The gas mixture to be reacted can also contain small amounts of alcohol ROH, for example 0 to 10 vol %, and small amounts of NO, for example 0 to 10 vol %, based in both cases on the total volume of the gas mixture to be used. Such additions of ROH or NO can originate for instance from the preparation of the alkyl nitrite and, for example, can be introduced with the latter into the reaction gas mixture.

In terms of the invention, halogen is fluorine, chlorine, bromine or iodine, preferably chlorine or bromine and particularly preferably chlorine.

The halogen can be metered into the reaction mixture as such, as a gas, either in the pure form or in a mixture with other gases, preferably in a mixture with an inert gas and particularly preferably in a mixture with nitrogen or carbon dioxide. However, it can also be metered into the reaction mixture in dissolved form, the solvent used preferably being one of the substances present in the reaction mixture, for example the alcohol corresponding to the alkyl nitrite.

The concentration of the halogen in the gas stream can be 1 to 1000 ppm (by volume), preferably 10 to 500 ppm (by volume).

EXAMPLE

Definitions

The space-time yield (STY) in [g/l×h] for dimethyl carbonate in the examples is calculated according to the equation $$STY = \frac{m_{DMC}}{V_{cat} \times t}$$

where $m_{DMC}$ is the amount of dimethyl carbonate (DMC) formed, $V_{cat}$ is the volume of catalyst charge and t is the time.

The selectivity S [%] is calculated according to the equation $$S = \frac{n_{DMC}}{n_{DMC} + 2 \times n_{DMO} + n_{MF} + n_{FDA}} \times 100[\%]$$

where $n_{DMC}$=amount of dimethyl carbonate $n_{DMO}$=amount of dimethyl oxalate $n_{MF}$=amount of methyl formate $n_{FDA}$=amount of formaldehyde dimethylacetal.

Preparation of the catalyst 100 ml of aluminium oxide pellets were impregnated with an aqueous solution of $Li_2PdCl_4$ and the product was dried at 80° C. under vacuum.

The catalyst then contained 8 g of Pd/l.

Description of the process 20 ml of the catalyst described were introduced into a vertical tubular reactor (glass, length 50 cm, diameter 4 cm) packed with Raschig rings.

The glass tube was heated to 90° C. and a gas mixture of 55 vol % of $N_2$, 20 vol % of methyl nitrite, 20 vol % of CO and 5 vol % of methanol was passed through, 100 ppm (by volume) of $Cl_2$ being added to this gas mixture.

The gas flowing out of the reactor was cooled to 5° C. and the condensed phase obtained was examined by gas chromatography.

The uncondensed products were determined by IR spectroscopy and mass spectroscopy.

Dimethyl carbonate was formed after 2 h with a space-time yield of STY=190 g/×h and a selectivity of S=99%.

Even after a reaction time of 60 h, the space-time yield was STY=190 g/l×h and the selectivity was S=99%.

What is claimed is:

1. A process for the preparation of a dialkyl carbonate of the formula $$O=C(OR)_2,$$

wherein

R represents linear of branched $C_1$–$C_4$-alkyl, by reacting carbon monoxide (CO) with an alkyl nitrite of the formula $$RONO,$$

wherein

R is as defined, in the presence of an inert gas, in the presence of the corresponding alcohol and in the presence or absence of NO, on a supported platinum metal catalyst, at elevated temperature in a continuous gas phase reaction, wherein the reaction is carried out at a volume ratio of alkyl nitrite:CO=0.1 to 10:1, a pressure of 0.5 to 10 bar, and a temperature of 50° to 170° C., element halogen being added batchwise or continuously.

2. The process of claim 1, wherein the catalyst is a supported palladium catalyst.

3. The process of claim 2, wherein the catalyst is a supported Pd(II) halide catalyst.

4. The process of claim 3, wherein the catalyst is a supported $PdCl_2$ catalyst.

5. The process of claim 1, wherein the volume ratio of alkyl nitrite:CO is 0.2 to 4:1.

6. The process of claim 5, wherein the volume ratio of alkyl nitrite:CO is 0.3 to 3:1.

7. The process of claim 1, wherein R is methyl or ethyl.

8. The process of claim 7, wherein R is methyl.

9. The process of claim 1, wherein the pressure is of from 0.8 to 7 bar.

10. The process of claim 9, wherein the pressure is of from 1 to 6 bar.

11. The process of claim 10, wherein the pressure is of from 1 to 5 bar.

12. The process of claim 1, wherein halogen is added in an amount such that the educt gas contains the halogen in a concentration of 1 to 1000 ppm by volume.

13. The process of claim 12, wherein halogen is added in an amount such that the educt gas contains the halogen in a concentration of 10 to 500 ppm by volume.

14. The process of claim 1, wherein chlorine or bromine is added.

15. The process of claim 14, wherein chlorine is added.

* * * * *